(12) United States Patent
Lashinski

(10) Patent No.: US 8,556,881 B2
(45) Date of Patent: *Oct. 15, 2013

(54) CATHETER GUIDANCE THROUGH A CALCIFIED AORTIC VALVE

(75) Inventor: Randall T. Lashinski, Santa Rosa, CA (US)

(73) Assignee: Direct Flow Medical, Inc., Santa Rosa, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/369,201

(22) Filed: Feb. 8, 2012

(65) Prior Publication Data

US 2012/0203263 A1 Aug. 9, 2012

Related U.S. Application Data

(63) Continuation of application No. 11/874,825, filed on Oct. 18, 2007, now Pat. No. 8,133,213.

(60) Provisional application No. 60/862,187, filed on Oct. 19, 2006.

(51) Int. Cl.
*A61M 31/00* (2006.01)

(52) U.S. Cl.
USPC ........... 604/510; 604/104; 604/509; 606/194; 623/2.11

(58) Field of Classification Search
USPC ................. 604/96.01–103.14, 104–109, 500, 604/507–510; 128/898; 606/191, 192, 194, 606/198; 623/1.11, 1.12, 1.26, 2.11
See application file for complete search history.

(56) References Cited

U.S. PATENT DOCUMENTS

| | | | |
|---|---|---|---|
| 3,416,562 | A | 12/1968 | Freeman et al. |
| 3,657,744 | A | 4/1972 | Ersek |
| 3,671,979 | A | 6/1972 | Moulopoulos |
| 3,714,671 | A | 2/1973 | Edwards |

(Continued)

FOREIGN PATENT DOCUMENTS

| | | |
|---|---|---|
| DE | 2700531 C2 | 4/1985 |
| EP | 2241284 A1 | 10/2010 |

(Continued)

OTHER PUBLICATIONS

David, et al.: Aortic valve replacement with the Toronto SPV bioprosthesis. J Heart Valve Dis, 1992; 244-248, vol. 1 No. 2.

(Continued)

*Primary Examiner* — Kami A Bosworth
(74) *Attorney, Agent, or Firm* — Knobbe, Martens, Olson & Bear, LLP

(57) ABSTRACT

A method of treating a patient with a calcified aortic valve includes introducing a guide wire into a blood vessel. The guide wire is advanced through the aorta to the aortic valve and then through the aortic valve. A balloon dilatation catheter is introduced into the blood vessel over the guide wire. The balloon dilatation catheter includes an elongate body, a distal portion, a guide wire lumen, an inflation lumen, and a dilatation balloon. The balloon dilatation catheter further includes at least one deflection wire lumen, and at least one deflection wire residing in the at least one deflection wire lumen and having a distal end attached to the distal portion. The balloon dilatation catheter is advanced over the guide wire through the aorta, through the aortic valve, and the dilatation balloon is inflated.

5 Claims, 10 Drawing Sheets

(56) References Cited

U.S. PATENT DOCUMENTS

| | | |
|---|---|---|
| 4,035,849 A | 7/1977 | Angell et al. |
| 4,056,854 A | 11/1977 | Boretos et al. |
| 4,106,129 A | 8/1978 | Caprentier et al. |
| 4,183,102 A | 1/1980 | Guiset |
| 4,213,207 A | 7/1980 | Wilson |
| 4,221,548 A | 9/1980 | Child |
| 4,339,831 A | 7/1982 | Johnson |
| 4,592,340 A | 6/1986 | Boyles |
| 4,612,011 A | 9/1986 | Kautzky |
| 4,652,263 A | 3/1987 | Herweck et al. |
| 4,662,885 A | 5/1987 | DiPisa, Jr. |
| 4,727,873 A | 3/1988 | Mobin-Uddin |
| 4,750,488 A | 6/1988 | Wuchinich et al. |
| 4,750,901 A | 6/1988 | Molteno |
| 4,781,682 A | 11/1988 | Patel |
| 4,787,899 A | 11/1988 | Lazarus |
| 4,817,600 A | 4/1989 | Herms et al. |
| 4,827,911 A | 5/1989 | Broadwin et al. |
| 4,892,541 A | 1/1990 | Alonso |
| 4,922,902 A | 5/1990 | Wuchinich et al. |
| 4,931,047 A | 6/1990 | Broadwin et al. |
| 4,955,856 A | 9/1990 | Phillips |
| 4,960,424 A | 10/1990 | Grooters |
| 4,994,077 A | 2/1991 | Dobben |
| 5,015,227 A | 5/1991 | Broadwin et al. |
| 5,026,383 A | 6/1991 | Nobles |
| 5,032,128 A | 7/1991 | Alonso |
| 5,151,105 A | 9/1992 | Kwan-Gett |
| 5,163,897 A | 11/1992 | Persky |
| 5,163,953 A | 11/1992 | Vince |
| 5,167,628 A | 12/1992 | Boyles |
| 5,207,695 A | 5/1993 | Trout, III |
| 5,269,784 A | 12/1993 | Mast |
| 5,330,528 A | 7/1994 | Lazim |
| 5,360,444 A | 11/1994 | Kusuhara |
| 5,370,685 A | 12/1994 | Stevens |
| 5,370,691 A | 12/1994 | Samson |
| 5,397,351 A | 3/1995 | Pavcnik et al. |
| 5,411,552 A | 5/1995 | Andersen et al. |
| 5,423,851 A | 6/1995 | Samuels |
| 5,443,499 A | 8/1995 | Schmitt |
| 5,449,385 A | 9/1995 | Religa et al. |
| 5,500,014 A | 3/1996 | Quijano et al. |
| 5,534,024 A | 7/1996 | Rogers et al. |
| 5,554,180 A | 9/1996 | Turk |
| 5,554,185 A | 9/1996 | Block et al. |
| 5,578,034 A | 11/1996 | Estes |
| 5,616,149 A | 4/1997 | Barath |
| 5,618,299 A | 4/1997 | Khosravi et al. |
| 5,649,978 A | 7/1997 | Samson |
| 5,690,570 A | 11/1997 | Chang et al. |
| 5,697,968 A | 12/1997 | Rogers et al. |
| 5,817,102 A | 10/1998 | Johnson et al. |
| 5,824,052 A | 10/1998 | Khosravi et al. |
| 5,824,053 A | 10/1998 | Khosravi et al. |
| 5,840,081 A | 11/1998 | Andersen et al. |
| 5,848,964 A | 12/1998 | Samuels |
| 5,855,601 A | 1/1999 | Bessler et al. |
| 5,871,537 A | 2/1999 | Holman et al. |
| 5,957,949 A | 9/1999 | Leonhardt et al. |
| 5,980,570 A | 11/1999 | Simpson |
| 6,007,575 A | 12/1999 | Samuels et al. |
| 6,090,139 A | 7/2000 | Lemelson |
| 6,090,140 A | 7/2000 | Gabbay |
| 6,102,944 A | 8/2000 | Huynh et al. |
| 6,110,201 A | 8/2000 | Quijano et al. |
| 6,117,106 A | 9/2000 | Wasicek et al. |
| 6,126,007 A | 10/2000 | Kari et al. |
| 6,156,062 A | 12/2000 | McGuinness |
| 6,168,614 B1 | 1/2001 | Andersen et al. |
| 6,196,996 B1 | 3/2001 | Teirstein |
| 6,221,096 B1 | 4/2001 | Aiba et al. |
| 6,280,412 B1 | 8/2001 | Pederson, Jr. et al. |
| 6,299,637 B1 | 10/2001 | Shaolian et al. |
| 6,309,399 B1 | 10/2001 | Barbut et al. |
| 6,312,462 B1 | 11/2001 | McDermott et al. |
| 6,312,465 B1 | 11/2001 | Griffin et al. |
| 6,319,276 B1 | 11/2001 | Holman et al. |
| 6,371,970 B1 | 4/2002 | Khosravi et al. |
| 6,371,983 B1 | 4/2002 | Lane |
| 6,395,019 B2 | 5/2002 | Chobotov |
| 6,395,026 B1 | 5/2002 | Aboul-Hosn et al. |
| 6,409,759 B1 | 6/2002 | Peredo |
| 6,425,916 B1 | 7/2002 | Garrison et al. |
| 6,440,164 B1 | 8/2002 | Di Matteo et al. |
| 6,458,156 B1 | 10/2002 | Wan et al. |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,544,291 B2 | 4/2003 | Taylor |
| 6,562,069 B2 | 5/2003 | Cai et al. |
| 6,572,652 B2 | 6/2003 | Shaknovich |
| 6,582,462 B1 | 6/2003 | Andersen et al. |
| 6,602,286 B1 | 8/2003 | Strecker |
| 6,676,698 B2 | 1/2004 | McGuckin, Jr. et al. |
| 6,682,543 B2 | 1/2004 | Barbut et al. |
| 6,692,512 B2 | 2/2004 | Jang |
| 6,692,523 B2 | 2/2004 | Holman et al. |
| 6,719,788 B2 | 4/2004 | Cox |
| 6,719,789 B2 | 4/2004 | Cox |
| 6,733,525 B2 | 5/2004 | Yang et al. |
| 6,736,845 B2 | 5/2004 | Marquez et al. |
| 6,755,811 B1 | 6/2004 | Constantz |
| 6,761,733 B2 | 7/2004 | Chobotov et al. |
| 6,764,494 B2 | 7/2004 | Menz et al. |
| 6,767,362 B2 | 7/2004 | Schreck |
| 6,769,434 B2 | 8/2004 | Liddicoat et al. |
| 6,827,735 B2 | 12/2004 | Greenberg |
| 6,875,212 B2 | 4/2005 | Shaolian et al. |
| 6,890,353 B2 | 5/2005 | Cohn et al. |
| 6,896,690 B1 | 5/2005 | Lambrecht et al. |
| 6,921,414 B2 | 7/2005 | Klumb et al. |
| 6,936,057 B1 | 8/2005 | Nobles |
| 6,949,122 B2 | 9/2005 | Adams et al. |
| 6,958,212 B1 | 10/2005 | Hubbell et al. |
| 6,974,476 B2 | 12/2005 | McGuckin, Jr. et al. |
| 6,989,027 B2 | 1/2006 | Allen et al. |
| 6,994,093 B2 | 2/2006 | Murphy et al. |
| 7,018,406 B2 | 3/2006 | Seguin et al. |
| 7,037,334 B1 | 5/2006 | Hlavka et al. |
| 7,052,410 B2 | 5/2006 | Cameron |
| 7,052,487 B2 | 5/2006 | Cohn et al. |
| 7,077,844 B2 | 7/2006 | Michelson |
| 7,077,862 B2 | 7/2006 | Vidlund et al. |
| 7,081,129 B2 | 7/2006 | Chobotov |
| 7,108,715 B2 | 9/2006 | Lawrence-Brown et al. |
| 7,112,219 B2 | 9/2006 | Vidlund et al. |
| 7,125,464 B2 | 10/2006 | Chobotov et al. |
| 7,150,758 B2 | 12/2006 | Kari et al. |
| 7,186,264 B2 | 3/2007 | Liddicoat et al. |
| 7,192,441 B2 | 3/2007 | Sherry |
| 7,201,772 B2 | 4/2007 | Schwammenthal et al. |
| 7,217,287 B2 | 5/2007 | Wilson et al. |
| 7,252,682 B2 | 8/2007 | Seguin |
| 7,255,711 B2 | 8/2007 | Holman et al. |
| 7,273,481 B2 | 9/2007 | Lombardo et al. |
| 7,276,078 B2 | 10/2007 | Spenser et al. |
| 7,309,340 B2 | 12/2007 | Fallin et al. |
| 7,320,704 B2 | 1/2008 | Lashinski et al. |
| 7,429,269 B2 | 9/2008 | Schwammenthal et al. |
| 7,435,257 B2 | 10/2008 | Lashinski et al. |
| 7,442,204 B2 | 10/2008 | Schwammenthal et al. |
| 7,445,630 B2 | 11/2008 | Lashinski et al. |
| 7,468,072 B2 | 12/2008 | Morsi |
| 7,491,230 B2 | 2/2009 | Holman et al. |
| 7,534,259 B2 | 5/2009 | Lashinski et al. |
| 7,534,261 B2 | 5/2009 | Friedman |
| 7,556,645 B2 | 7/2009 | Lashinski et al. |
| 7,556,646 B2 | 7/2009 | Yang et al. |
| 7,585,321 B2 | 9/2009 | Cribier |
| 7,615,071 B2 | 11/2009 | Chobotov |
| 7,628,805 B2 | 12/2009 | Bash et al. |
| 7,641,686 B2 | 1/2010 | Lashinski et al. |
| 7,658,762 B2 | 2/2010 | Lashinski et al. |

(56) References Cited

U.S. PATENT DOCUMENTS

| | | |
|---|---|---|
| 7,666,193 B2 | 2/2010 | Starksen et al. |
| 7,666,220 B2 | 2/2010 | Evans et al. |
| 7,678,217 B2 | 3/2010 | Chobotov et al. |
| 7,682,383 B2 | 3/2010 | Robin |
| 7,726,943 B2 | 6/2010 | Stommel |
| 7,731,741 B2 | 6/2010 | Eidenschink |
| 7,744,912 B1 | 6/2010 | Hubbell |
| 7,766,954 B2 | 8/2010 | Chobotov et al. |
| 7,780,726 B2 | 8/2010 | Seguin |
| 7,785,365 B2 | 8/2010 | Holman et al. |
| 7,799,068 B2 | 9/2010 | Holman et al. |
| 7,824,442 B2 | 11/2010 | Salahieh et al. |
| 7,846,203 B2 | 12/2010 | Cribier |
| 7,935,144 B2 | 5/2011 | Robin et al. |
| 8,002,826 B2 | 8/2011 | Seguin |
| 8,012,201 B2 | 9/2011 | Lashinski et al. |
| 8,016,877 B2 | 9/2011 | Seguin et al. |
| 8,057,540 B2 | 11/2011 | Cribier et al. |
| 8,070,805 B2 | 12/2011 | Vidlund et al. |
| 8,092,525 B2 | 1/2012 | Eliasen et al. |
| 8,133,213 B2 | 3/2012 | Lashinski |
| 8,142,497 B2 | 3/2012 | Friedman |
| 8,167,932 B2 * | 5/2012 | Bourang et al. ............ 623/2.11 |
| 8,197,534 B2 | 6/2012 | Brumleve et al. |
| 2001/0007956 A1 | 7/2001 | Letac et al. |
| 2001/0010017 A1 | 7/2001 | Letac et al. |
| 2001/0021872 A1 | 9/2001 | Bailey et al. |
| 2002/0082689 A1 | 6/2002 | Chinn |
| 2002/0095116 A1 | 7/2002 | Strecter |
| 2002/0123802 A1 | 9/2002 | Snyders |
| 2002/0151961 A1 | 10/2002 | Lashinski et al. |
| 2002/0151970 A1 | 10/2002 | Garrison et al. |
| 2002/0183838 A1 | 12/2002 | Liddicoat et al. |
| 2002/0183841 A1 | 12/2002 | Cohn et al. |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0027332 A1 | 2/2003 | Lafrance et al. |
| 2003/0036795 A1 | 2/2003 | Andersen et al. |
| 2003/0040772 A1 | 2/2003 | Hyodoh et al. |
| 2003/0055495 A1 | 3/2003 | Pease et al. |
| 2003/0055496 A1 | 3/2003 | Cai et al. |
| 2003/0074058 A1 | 4/2003 | Sherry |
| 2003/0078654 A1 | 4/2003 | Taylor et al. |
| 2003/0083538 A1 | 5/2003 | Adams et al. |
| 2003/0093145 A1 | 5/2003 | Lawrence-Brown et al. |
| 2003/0125793 A1 | 7/2003 | Vesely |
| 2003/0125797 A1 | 7/2003 | Chobotov et al. |
| 2003/0130730 A1 | 7/2003 | Cohn et al. |
| 2003/0130731 A1 | 7/2003 | Vidlund et al. |
| 2003/0191527 A1 | 10/2003 | Shaknovich |
| 2003/0220684 A1 | 11/2003 | Holman et al. |
| 2003/0225453 A1 | 12/2003 | Murch |
| 2003/0233022 A1 | 12/2003 | Vidlund et al. |
| 2004/0003819 A1 | 1/2004 | St. Goar et al. |
| 2004/0030381 A1 | 2/2004 | Shu |
| 2004/0030382 A1 | 2/2004 | St. Goar et al. |
| 2004/0034320 A1 | 2/2004 | Burnett |
| 2004/0039442 A1 | 2/2004 | St. Goar et al. |
| 2004/0059412 A1 * | 3/2004 | Lytle et al. ................ 623/2.11 |
| 2004/0087975 A1 | 5/2004 | Lucatero et al. |
| 2004/0093060 A1 | 5/2004 | Seguin et al. |
| 2004/0116951 A1 | 6/2004 | Rosengart |
| 2004/0127979 A1 | 7/2004 | Wilson et al. |
| 2004/0148019 A1 | 7/2004 | Vidlund et al. |
| 2004/0148020 A1 | 7/2004 | Vidlund et al. |
| 2004/0167620 A1 | 8/2004 | Ortiz et al. |
| 2004/0176836 A1 | 9/2004 | Kari et al. |
| 2004/0186563 A1 | 9/2004 | Lobbi |
| 2004/0210304 A1 | 10/2004 | Seguin et al. |
| 2004/0225354 A1 | 11/2004 | Allen et al. |
| 2004/0249413 A1 | 12/2004 | Allen et al. |
| 2004/0249452 A1 | 12/2004 | Adams et al. |
| 2004/0254600 A1 | 12/2004 | Zarbatany et al. |
| 2004/0260322 A1 | 12/2004 | Rudko et al. |
| 2004/0260390 A1 | 12/2004 | Sarac et al. |
| 2005/0004654 A1 | 1/2005 | Khosravi et al. |
| 2005/0010285 A1 | 1/2005 | Lambrecht et al. |
| 2005/0021056 A1 | 1/2005 | St. Goar et al. |
| 2005/0021057 A1 | 1/2005 | St. Goar et al. |
| 2005/0021128 A1 | 1/2005 | Nakahama et al. |
| 2005/0033446 A1 | 2/2005 | Deem et al. |
| 2005/0055082 A1 | 3/2005 | Ben Muvhar et al. |
| 2005/0065550 A1 | 3/2005 | Starksen et al. |
| 2005/0090846 A1 | 4/2005 | Pedersen et al. |
| 2005/0107810 A1 | 5/2005 | Morales et al. |
| 2005/0131528 A1 | 6/2005 | Buscemit et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137695 A1 | 6/2005 | Salahieh et al. |
| 2005/0137696 A1 | 6/2005 | Salahieh et al. |
| 2005/0137699 A1 | 6/2005 | Salahieh et al. |
| 2005/0137701 A1 | 6/2005 | Salahieh et al. |
| 2005/0203549 A1 | 9/2005 | Realyvasquez |
| 2005/0203614 A1 | 9/2005 | Forster et al. |
| 2005/0209674 A1 | 9/2005 | Kutscher et al. |
| 2005/0209687 A1 | 9/2005 | Sitzmann et al. |
| 2005/0222488 A1 | 10/2005 | Rahdert et al. |
| 2005/0222489 A1 | 10/2005 | Rahdert et al. |
| 2005/0228422 A1 | 10/2005 | Rahdert et al. |
| 2005/0251251 A1 | 11/2005 | Cribier |
| 2005/0267574 A1 | 12/2005 | Cohn et al. |
| 2005/0273160 A1 | 12/2005 | Lashinski et al. |
| 2006/0004442 A1 | 1/2006 | Spenser et al. |
| 2006/0020327 A1 | 1/2006 | Lashinski et al. |
| 2006/0020332 A1 | 1/2006 | Lashinski et al. |
| 2006/0020333 A1 | 1/2006 | Lashinski et al. |
| 2006/0020334 A1 | 1/2006 | Lashinski et al. |
| 2006/0025750 A1 | 2/2006 | Starksen et al. |
| 2006/0025787 A1 | 2/2006 | Morales et al. |
| 2006/0025854 A1 | 2/2006 | Lashinski et al. |
| 2006/0025855 A1 | 2/2006 | Lashinski et al. |
| 2006/0041306 A1 | 2/2006 | Vidlund et al. |
| 2006/0063970 A1 | 3/2006 | Raman et al. |
| 2006/0074485 A1 | 4/2006 | Realyvasquez |
| 2006/0100699 A1 | 5/2006 | Vidlund et al. |
| 2006/0106449 A1 | 5/2006 | Ben Muvhar |
| 2006/0106450 A1 | 5/2006 | Ben Muvhar |
| 2006/0129025 A1 | 6/2006 | Levine et al. |
| 2006/0129051 A1 | 6/2006 | Rowe et al. |
| 2006/0129235 A1 | 6/2006 | Seguin et al. |
| 2006/0149135 A1 | 7/2006 | Paz |
| 2006/0178700 A1 | 8/2006 | Quinn |
| 2006/0190030 A1 | 8/2006 | To et al. |
| 2006/0212112 A1 | 9/2006 | Evans et al. |
| 2006/0217637 A1 | 9/2006 | Leiboff et al. |
| 2006/0229717 A1 | 10/2006 | Cohn et al. |
| 2006/0235512 A1 | 10/2006 | Osborne et al. |
| 2006/0241656 A1 | 10/2006 | Starksen et al. |
| 2006/0252984 A1 | 11/2006 | Rahdert et al. |
| 2006/0271172 A1 | 11/2006 | Tehrani |
| 2006/0276874 A1 | 12/2006 | Wilson et al. |
| 2006/0276881 A1 | 12/2006 | Holman et al. |
| 2007/0005133 A1 | 1/2007 | Lashinski et al. |
| 2007/0027536 A1 | 2/2007 | Mihaljevic |
| 2007/0038293 A1 | 2/2007 | St. Goar et al. |
| 2007/0043435 A1 | 2/2007 | Seguin et al. |
| 2007/0050022 A1 | 3/2007 | Vidlund et al. |
| 2007/0055356 A1 | 3/2007 | Eidenschink |
| 2007/0093890 A1 | 4/2007 | Eliasen et al. |
| 2007/0142906 A1 | 6/2007 | Figulla et al. |
| 2007/0185566 A1 | 8/2007 | Khitin et al. |
| 2007/0185571 A1 | 8/2007 | Kapadia et al. |
| 2007/0203575 A1 | 8/2007 | Forster et al. |
| 2007/0213814 A1 | 9/2007 | Liddicoat et al. |
| 2007/0255399 A1 | 11/2007 | Eliasen et al. |
| 2007/0265700 A1 | 11/2007 | Eliasen et al. |
| 2007/0293943 A1 | 12/2007 | Quinn |
| 2008/0015687 A1 | 1/2008 | Lashinski et al. |

(56) References Cited

U.S. PATENT DOCUMENTS

| | | |
|---|---|---|
| 2008/0039881 A1 | 2/2008 | Greenberg |
| 2008/0039923 A1 | 2/2008 | Taylor et al. |
| 2008/0039935 A1 | 2/2008 | Buch et al. |
| 2008/0109073 A1 | 5/2008 | Lashinski et al. |
| 2008/0125860 A1 | 5/2008 | Webler et al. |
| 2008/0188923 A1 | 8/2008 | Chu |
| 2008/0194905 A1 | 8/2008 | Walsh |
| 2008/0208329 A1 | 8/2008 | Bishop et al. |
| 2008/0215143 A1 | 9/2008 | Seguin |
| 2009/0043382 A1 | 2/2009 | Maurer et al. |
| 2009/0048668 A1 | 2/2009 | Wilson et al. |
| 2009/0076600 A1 | 3/2009 | Quinn |
| 2009/0082857 A1 | 3/2009 | Lashinski et al. |
| 2009/0088836 A1 | 4/2009 | Bishop et al. |
| 2009/0131849 A1 | 5/2009 | Maurer et al. |
| 2009/0149949 A1 | 6/2009 | Quinn |
| 2009/0222084 A1 | 9/2009 | Friedman |
| 2009/0264984 A1 | 10/2009 | Chobotov |
| 2009/0318949 A1 | 12/2009 | Ganpath et al. |
| 2009/0319029 A1 | 12/2009 | Evans et al. |
| 2010/0004728 A1 | 1/2010 | Rao et al. |
| 2010/0010623 A1 | 1/2010 | Lashinski et al. |
| 2010/0016942 A1 | 1/2010 | Chobotov et al. |
| 2010/0016948 A1 | 1/2010 | Chobotov |
| 2010/0030204 A1 | 2/2010 | Stein et al. |
| 2010/0030327 A1 | 2/2010 | Chatel |
| 2010/0036360 A1 | 2/2010 | Herbowy et al. |
| 2010/0036485 A1 | 2/2010 | Seguin |
| 2010/0076481 A1 | 3/2010 | Stephens et al. |
| 2010/0106087 A1 | 4/2010 | Evans et al. |
| 2010/0168844 A1 | 7/2010 | Toomes et al. |
| 2010/0256754 A1 | 10/2010 | Styrc |
| 2010/0292772 A1 | 11/2010 | Samuels |
| 2010/0324668 A1 | 12/2010 | Maurer et al. |
| 2011/0060407 A1 | 3/2011 | Ketai et al. |
| 2011/0066233 A1 | 3/2011 | Thornton et al. |
| 2011/0098802 A1 | 4/2011 | Braido et al. |
| 2011/0112625 A1 | 5/2011 | Ben-Muvhar et al. |
| 2011/0153009 A1 | 6/2011 | Navia et al. |
| 2011/0160846 A1 | 6/2011 | Bishop et al. |
| 2011/0213460 A1 | 9/2011 | Lashinski et al. |
| 2012/0016468 A1 | 1/2012 | Robin et al. |
| 2012/0022629 A1 | 1/2012 | Perera et al. |
| 2013/0041458 A1 | 2/2013 | Lashinski et al. |

FOREIGN PATENT DOCUMENTS

| | | |
|---|---|---|
| WO | WO 91/17720 | 11/1991 |
| WO | WO 93/01768 | 2/1993 |
| WO | WO 96/02212 | 2/1996 |
| WO | WO 97/09947 A1 | 3/1997 |
| WO | WO98/55047 | 12/1998 |
| WO | WO 00/41652 | 7/2000 |
| WO | WO 00/42950 | 7/2000 |
| WO | WO 01/06959 | 2/2001 |
| WO | WO 03/063740 | 8/2003 |
| WO | WO 03/096932 A1 | 11/2003 |
| WO | WO 2005/087140 A1 | 9/2005 |
| WO | WO 2005/107650 A2 | 11/2005 |
| WO | WO 2009/144463 | 12/2009 |
| WO | WO2010/008548 | 1/2010 |
| WO | WO 2010/117367 A1 | 10/2010 |
| WO | WO 2011/033427 A1 | 3/2011 |
| WO | WO 2011/035154 | 3/2011 |
| WO | WO 2011/105979 A1 | 9/2011 |
| WO | WO 2012/024428 | 2/2012 |

OTHER PUBLICATIONS

European Examination Report for Application No. EP05770163.3 filed Jun. 7, 2006, dated Aug. 21, 2009 in 4 pages.

International Search Report for PCT Application No. PCT/US2005/015617 (the PCT counterpart of the parent application) filed May 5, 2005, mailed on Oct. 31, 2005.

International Search Report for PCT Application No. PCT/US2008/74104 filed Aug. 22, 2008, mailed on Dec. 24, 2008, in 3 pages.

Narendra Vyavahare et al., Prevention of Bioprosthetic Heart Valve Calcification by Ethanol Preincubation; American Heart Association, Inc., 1997, pp. 479-488, vol. 95.

U.S. Appl. No. 09/496,231, Jeffrey Hubbell et al., Biomaterials Formed by Nucleophilic Addition Reaction to Conjugated Unsaturated Groups, filed Feb. 1, 2000.

Written Opinion of International Searching Authority for PCT Application No. PCT/US2005/0156617, filed May 5, 2005.

Written Opinion of the International Searching Authority for Application No. PCT/US2008/74104 filed Aug. 22, 2008, mailed on Dec. 24, 2008, in 7 pages.

* cited by examiner

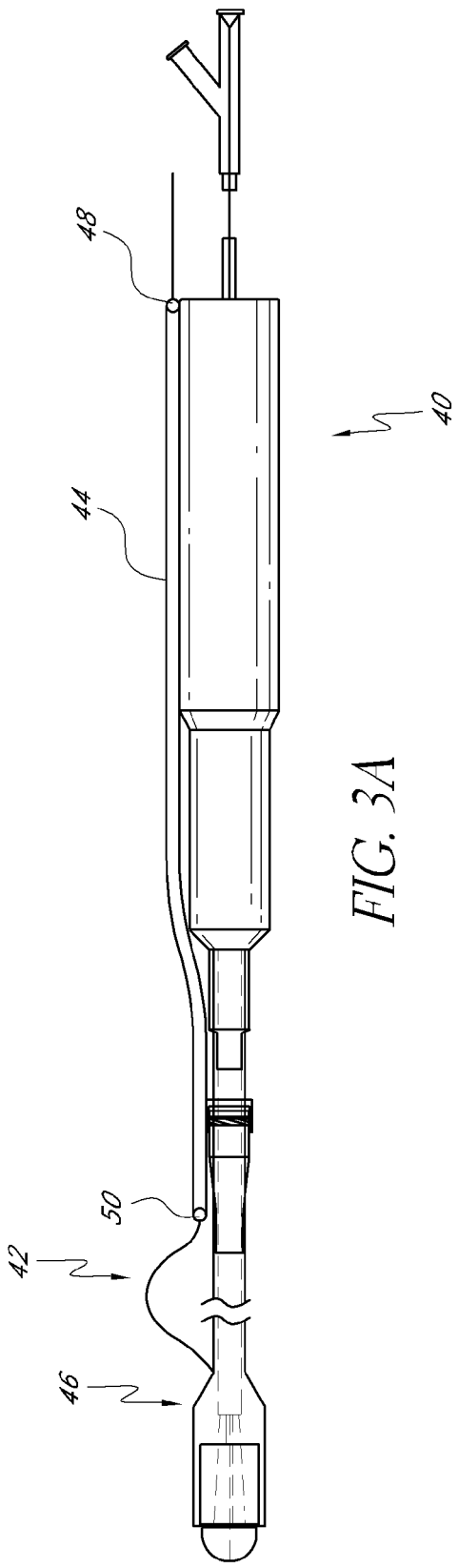
*FIG. 3A*
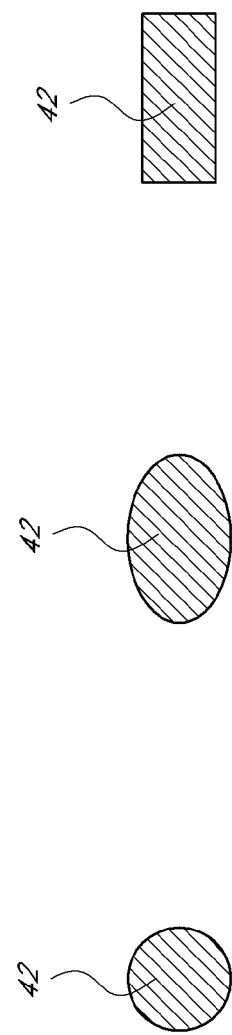
*FIG. 3C*  *FIG. 3D*  *FIG. 3E*

CATHETER GUIDANCE THROUGH A CALCIFIED AORTIC VALVE

CROSS-REFERENCE TO RELATED APPLICATIONS

This application is a continuation of U.S. patent application Ser. No. 11/874,825, filed Oct. 18, 2007, now U.S. Pat. No. 8,133,213, which claims the priority benefit of U.S. Provisional No. 60/862,187 filed Oct. 19, 2006, the entire disclosure of both priority documents is hereby incorporated by reference in its entirety.

BACKGROUND OF THE INVENTION

1. Field of the Invention

The present invention relates to medical methods and devices, and, in particular, to methods and devices for guiding a catheter through an aortic valve.

2. Description of the Related Art

According to recent estimates, more than 79,000 patients are diagnosed with aortic and mitral valve disease in U.S. hospitals each year. More than 49,000 mitral valve or aortic valve replacement procedures are performed annually in the U.S., along with a significant number of heart valve repair procedures.

The circulatory system is a closed loop bed of arterial and venous vessels supplying oxygen and nutrients to the body extremities through capillary beds. The driver of the system is the heart providing correct pressures to the circulatory system and regulating flow volumes as the body demands. Deoxygenated blood enters heart first through the right atrium and is allowed to the right ventricle through the tricuspid valve. Once in the right ventricle, the heart delivers this blood through the pulmonary valve and to the lungs for a gaseous exchange of oxygen. The circulatory pressures carry this blood back to the heart via the pulmonary veins and into the left atrium. Filling of the left atrium occurs as the mitral valve opens allowing blood to be drawn into the left ventricle for expulsion through the aortic valve and on to the body extremities. When the heart fails to continuously produce normal flow and pressures, a disease commonly referred to as heart failure occurs.

Heart failure simply defined is the inability for the heart to produce output sufficient to demand. Mechanical complications of heart failure include free-wall rupture, septal-rupture, papillary rupture or dysfunction aortic insufficiency and tamponade. Mitral, aortic or pulmonary valve disorders lead to a host of other conditions and complications exacerbating heart failure further. Other disorders include coronary disease, hypertension, and a diverse group of muscle diseases referred to as cardiomyopothies. Because of this syndrome establishes a number of cycles, heart failure begets more heart failure.

Heart failure as defined by the New York Heart Association in a functional classification.

I. Patients with cardiac disease but without resulting limitations of physical activity. Ordinary physical activity does not cause undue fatigue, palpitation, dyspnea, or anginal pain.

II. Patient with cardiac disease resulting in slight limitation of physical activity. These patients are comfortable at rest. Ordinary physical activity results in fatigue, palpitation, dyspnea, or anginal pain.

III. Patients with cardiac disease resulting in marked limitation of physical activity. These patients are comfortable at rest. Less than ordinary physical activity causes fatigue palpitation, dyspnea, or anginal pain.

IV. Patients with cardiac disease resulting in inability to carry on any physical activity without discomfort. Symptoms of cardiac insufficiency or of the anginal syndrome may be present even at rest. If any physical activity is undertaken, discomfort is increased.

There are many styles of mechanical valves that utilize both polymer and metallic materials. These include single leaflet, double leaflet, ball and cage style, slit-type and emulated polymer tricuspid valves. Though many forms of valves exist, the function of the valve is to control flow through a conduit or chamber. Each style will be best suited to the application or location in the body it was designed for.

Bioprosthetic heart valves comprise valve leaflets formed of flexible biological material. Bioprosthetic valves or components from human donors are referred to as homografts and xenografts are from non-human animal donors. These valves as a group are known as tissue valves. This tissue may include donor valve leaflets or other biological materials such as bovine pericardium. The leaflets are sewn into place and to each other to create a new valve structure. This structure may be attached to a second structure such as a stent or cage or other prosthesis for implantation to the body conduit.

Implantation of valves into the body has been accomplished by a surgical procedure and has been attempted via percutaneous method such as a catheterization or delivery mechanism utilizing the vasculature pathways. Surgical implantation of valves to replace or repair existing valves structures include the four major heart valves (tricuspid, pulmonary, mitral, aortic) and some venous valves in the lower extremities for the treatment of chronic venous insufficiency. Implantation includes the sewing of a new valve to the existing tissue structure for securement. Access to these sites generally include a thoracotomy or a sternotomy for the patient and include a great deal of recovery time. An open-heart procedure can include placing the patient on heart bypass to continue blood flow to vital organs such as the brain during the surgery. The bypass pump will continue to oxygenate and pump blood to the body's extremities while the heart is stopped and the valve is replaced. The valve may replace in whole or repair defects in the patient's current native valve. The device may be implanted in a conduit or other structure such as the heart proper or supporting tissue surrounding the heart. Attachments methods may include suturing, hooks or barbs, interference mechanical methods or an adhesion median between the implant and tissue.

Although valve repair and replacement can successfully treat many patients with valvular insufficiency, techniques currently in use are attended by significant morbidity and mortality. Most valve repair and replacement procedures require a thoracotomy, usually in the form of a median sternotomy, to gain access into the patient's thoracic cavity. A saw or other cutting instrument is used to cut the sternum longitudinally, allowing the two opposing halves of the anterior or ventral portion of the rib cage to be spread apart. A large opening into the thoracic cavity is thus created, through which the surgical team may directly visualize and operate upon the heart and other thoracic contents. Alternatively, a thoracotomy may be performed on a lateral side of the chest, wherein a large incision is made generally parallel to the ribs, and the ribs are spread apart and/or removed in the region of the incision to create a large enough opening to facilitate the surgery.

Surgical intervention within the heart generally requires isolation of the heart and coronary blood vessels from the remainder of the arterial system, and arrest of cardiac function. Usually, the heart is isolated from the arterial system by introducing an external aortic cross-clamp through a sternotomy and applying it to the aorta to occlude the aortic lumen between the brachiocephalic artery and the coronary ostia. Cardioplegic fluid is then injected into the coronary arteries, either directly into the coronary ostia or through a puncture in the ascending aorta, to arrest cardiac function. The patient is placed on extracorporeal cardiopulmonary bypass to maintain peripheral circulation of oxygenated blood.

Since surgical techniques are highly invasive and in the instance of a heart valve, the patient must be put on bypass during the operation, the need for a less invasive method of heart valve replacement has long been recognized.

SUMMARY OF THE INVENTION

One embodiment of the present invention comprises a method of treating a patient with a calcified aortic valve. The method comprises introducing a guide wire into a blood vessel. The guide wire is advanced through the aorta to the aortic valve and then through the aortic valve. A balloon dilatation catheter is introduced into the blood vessel over the guide wire.

The balloon dilatation catheter comprises an elongate body, a distal portion, a guide wire lumen, an inflation lumen, and a dilatation balloon. The balloon dilatation catheter further comprising at least one deflection wire lumen, the at least one deflection wire lumen having a distal opening proximal the distal portion, and at least one deflection wire residing in the at least one deflection wire lumen and having a distal end attached to the distal portion.

The balloon dilatation catheter is advanced over the guide wire through the aorta. The deflection wire is pushed towards the distal portion so that the deflection wire bows outward. The balloon dilatation catheter is advanced through the aortic valve, and the dilatation balloon is inflated.

Another embodiment of the present invention comprises a method of treating a patient with a calcified aortic valve. The method comprises introducing a guide wire into a blood vessel. The guide wire is advanced through the aorta to the aortic valve. The guide wire is advanced through the aortic valve. A balloon dilatation catheter is introduced into the blood vessel over the guide wire.

The balloon dilation catheter comprises an elongate body, a distal portion, a guide wire lumen, a dilatation balloon, and a first inflation lumen for inflating the dilation balloon. The balloon dilation catheter further comprises at least one displacement balloon located on the distal portion, and a second inflation lumen for inflating the at least one displacement balloon.

The balloon dilatation catheter is advanced over the guide wire through the aorta. The at least one displacement balloon is inflated. The balloon dilatation catheter is advanced through the aortic valve. The dilatation balloon is inflated.

Further features and advantages of the present invention will become apparent from the detailed description of preferred embodiments which follows, when considered together with the attached drawings and claims.

BRIEF DESCRIPTION OF THE DRAWINGS

FIG. 3A is side view of a catheter with a deflection wire.

FIG. 3C is a cross-sectional view of a deflection wire with a circular cross-section.

FIG. 3D is a cross-sectional view of a deflection wire with an oblong cross-section.

FIG. 3E is a cross-sectional view of a deflection wire with a rectangular cross-section.

DETAILED DESCRIPTION OF THE PREFERRED EMBODIMENT

Figure 1B:
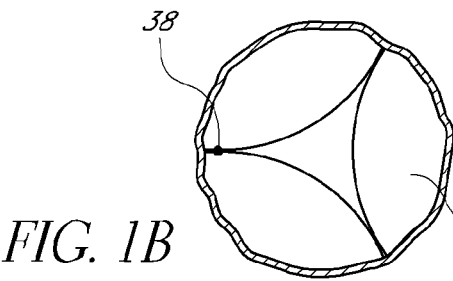
FIG. 1B is an exploded view of the aortic valve showing the position of the guide wire with respect to the aortic valve leaflets.
Figure 1A:
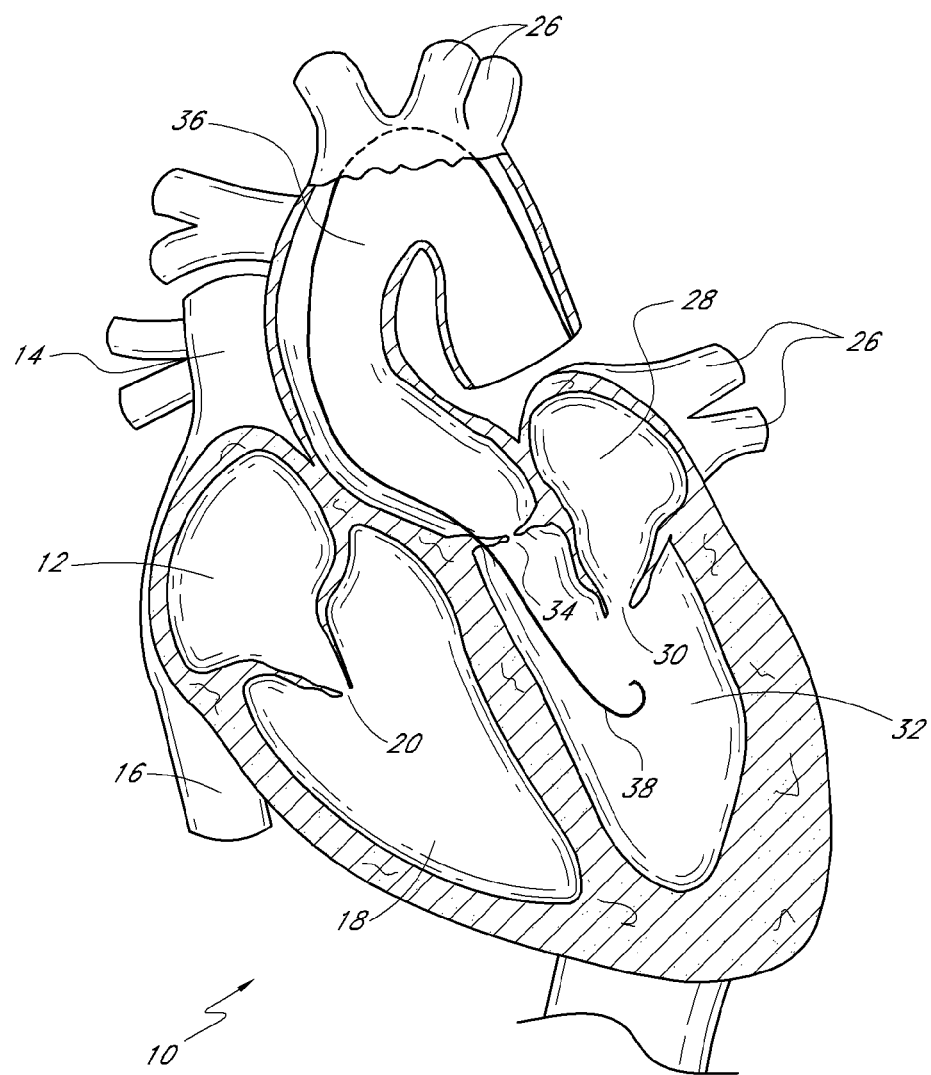
FIG. 1A is a cross-sectional schematic view of a heart and its major blood vessels with a guide wire disposed within the aorta and heart.

FIG. 1A is a schematic cross-sectional illustration of the anatomical structure and major blood vessels of a heart 10. Deoxygenated blood is delivered to the right atrium 12 of the heart 10 by the superior and inferior vena cava 14, 16. Blood in the right atrium 12 is allowed into the right ventricle 18 through the tricuspid valve 20. Once in the right ventricle 18, the heart 10 delivers this blood through the pulmonary valve to the pulmonary arteries and to the lungs for a gaseous exchange of oxygen. The circulatory pressures carry this blood back to the heart 10 via the pulmonary veins 26 and into the left atrium 28. Filling of the left ventricle 32 occurs as the mitral valve 30 opens allowing blood to be drawn into the left ventricle 32 for expulsion through the aortic valve 34 and on to the body extremities through the aorta 36. When the heart 10 fails to continuously produce normal flow and pressures, a disease commonly referred to as heart failure occurs.

One cause of heart failure is failure or malfunction of one or more of the valves of the heart 10. For example, the aortic valve 34 can malfunction for several reasons. For example, the aortic valve 34 may be abnormal from birth (e.g., bicuspid, calcification, congenital aortic valve disease), or it could become diseased with age (e.g., acquired aortic valve disease). In such situations, it can be desirable to replace the abnormal or diseased aortic valve 34.

For example, treatment of a calcified aortic valve 34 can be accomplished using minimally invasive procedures, such as balloon catheter dilatation. The balloon catheter described herein, in certain embodiments, generally has at least an elongate body, a guide wire lumen, an inflation lumen, and a dilatation balloon located on a distal portion of the balloon catheter. As illustrated in FIG. 1A, in one embodiment a guide wire 38 is inserted into the femoral artery and traverses the aorta 36 in a retrograde direction to the aortic valve 34. Because the guide wire 38 is flexible but is generally straight in the longitudinal direction, the guide wire 38 has a tendency to push against the vessel wall as the guide wire 38 is advanced through the aorta 36. As illustrated in FIG. 1B, this can result in the guide wire 38 passing through a commissural point of the aortic valve 34 near the vessel wall rather than the central lumen of the aortic valve 34.

After the guide wire 38 is in place through the aortic valve, a balloon catheter is advanced over the guide wire 38 to the aortic valve 34. If the guide wire 38 is positioned in a commissural point rather than the central lumen, then the balloon catheter will be required to also pass through the commissural point in order to traverse the aortic valve 34. However, because the balloon catheter has a larger diameter than the guide wire 38, the balloon catheter may abut against portions of the calcified aortic valve 34 leaflets, which will tend to impede passage of the balloon catheter through the aortic valve 34. This is especially problematic when the commissures of the calcified aortic valve 34 are fused, thereby further resisting passage of the balloon catheter through the aortic valve 34.

Figure 2B:
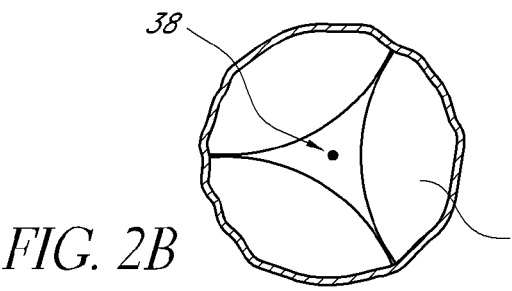
FIG. 2B is an exploded view of the aortic valve showing the position of the modified guide wire with respect to the aortic valve leaflets.
Figure 2A:
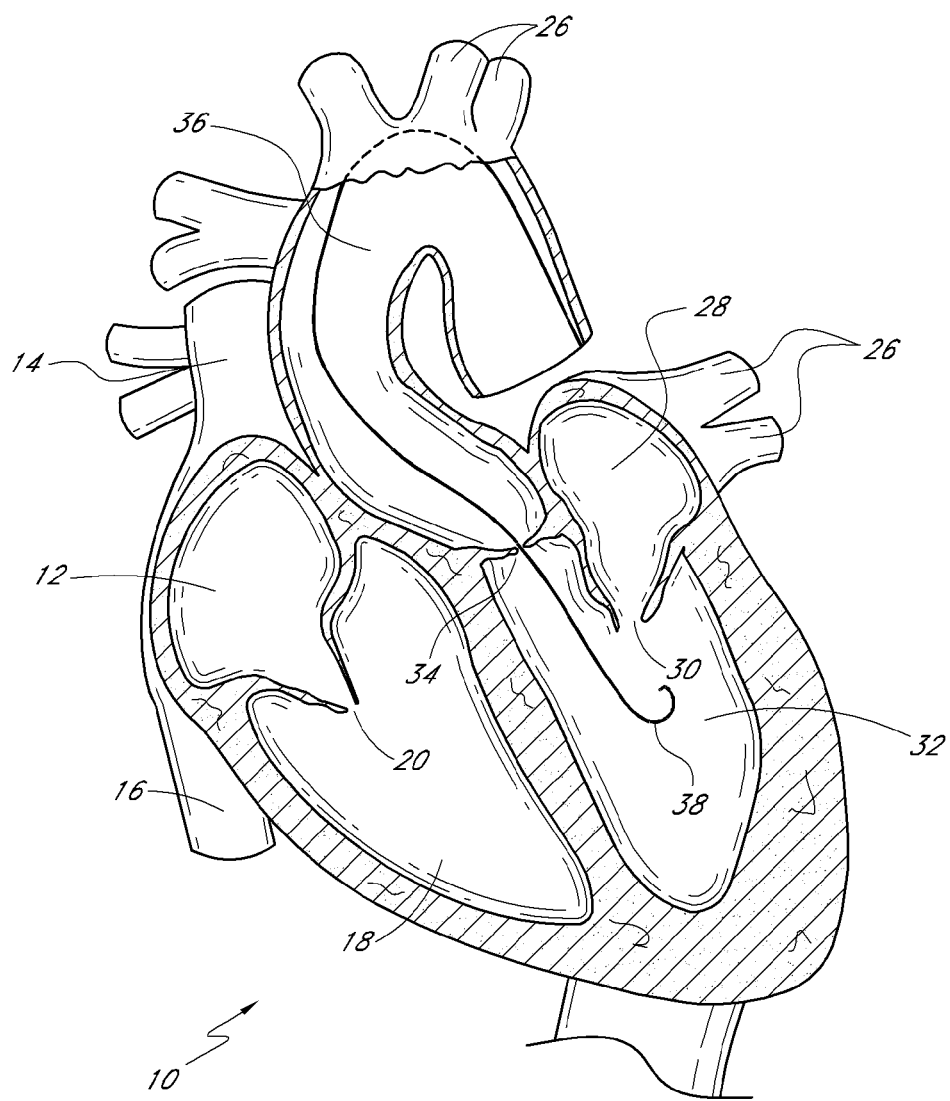
FIG. 2A is a cross-sectional schematic view of a heart and its major blood vessels with a modified guide wire disposed within the aorta and heart.

Therefore, in order to facilitate passage of the balloon catheter or any other catheter through the aortic valve 34, the catheter and guide wire 38 preferably should pass through the central lumen of the aortic valve 34 as illustrated in FIGS. 2A and 2B. As will be explained in detail below, this can be accomplished by pushing or displacing the catheter away from the vessel wall near the aortic valve 34 using certain techniques, methods and apparatus disclosed herein.

One method of displacing the catheter away from the vessel wall is to use a deflection member that is incorporated with the catheter. The deflection member can be configured to have a first position in which at least a portion of the deflection member is positioned near a longitudinal axis of the catheter and a second position in which a portion of the deflection member is moved away from the longitudinal axis of the catheter. In some embodiments, the deflection member can be, for example, a wire, a balloon, or a lever. FIG. 3A illustrates an embodiment of a catheter 40 having a deflection wire 42. The distal end or a distal portion of the deflection wire 42 is attached to a distal portion 46 of the catheter 40. The catheter 40 also has a deflection wire lumen 44 in which a portion of the deflection wire 42 resides. The deflection wire lumen 44 can have a proximal opening 48 and a distal opening 50 that is proximal the distal portion 46 where the deflection wire 42 is attached. A portion of the deflection wire 42 distal the distal opening 50 is uncovered and exposed.

Figure 3B:
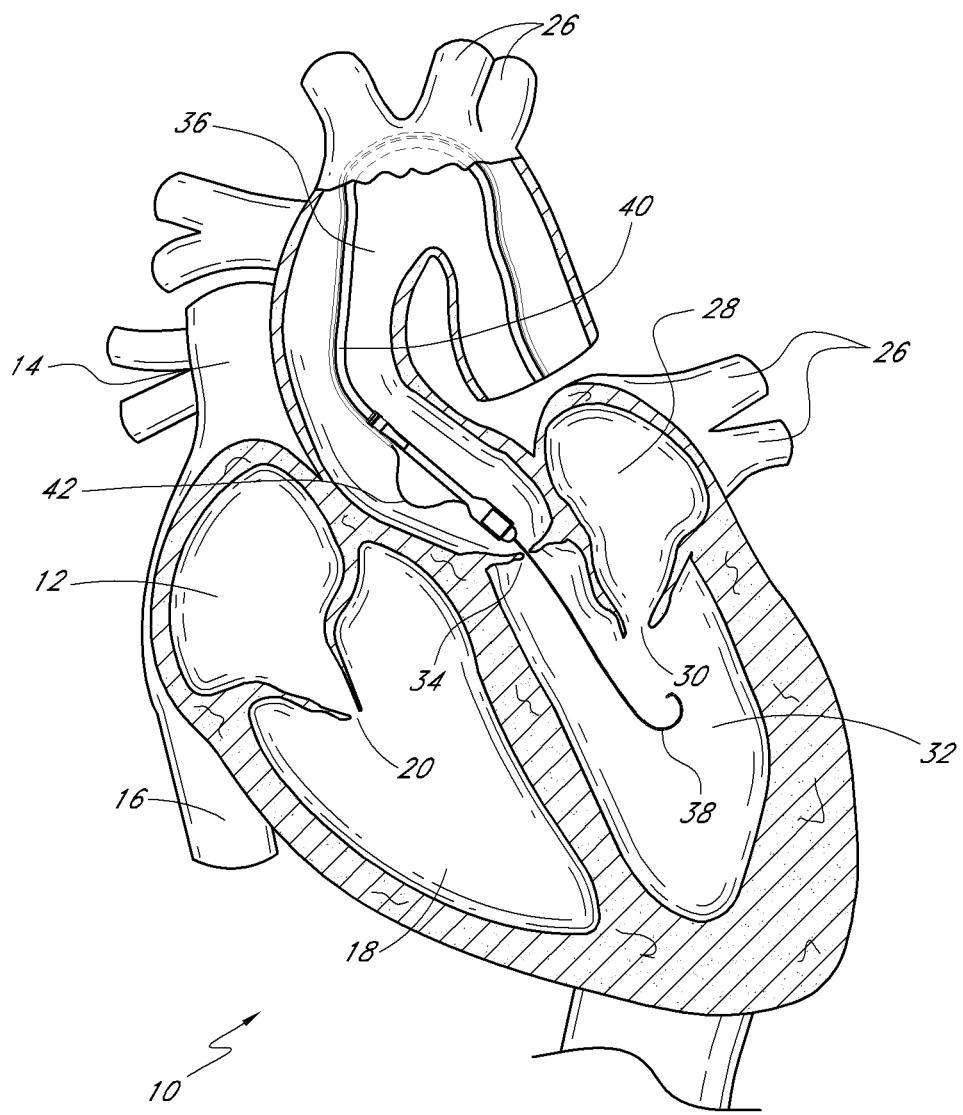
FIG. 3B is a cross-sectional view of a heart and its major blood vessels with a catheter disposed within the aorta and heart, the catheter centered within the aorta with a deflection wire.

The catheter 40 can be displaced from the vessel wall by pushing the deflection wire 42 towards the distal end of the catheter 40. As the deflection wire 42 is advanced towards the distal end of the catheter 40, the exposed portion of the deflection wire 42 distal the distal opening 50 will bow outwards and displace the catheter 40 and guide wire 38 away from the vessel wall and to the central lumen as illustrated in FIGS. 3A and 3B. If the deflection wire 42 is facing the center of the vessel rather than the vessel wall, the catheter 40 can be rotated so that the deflection wire 42 is facing the vessel wall and be capable of displacing the catheter when the deflection wire 42 is distally advanced.

In other embodiments, the catheter 40 has a plurality of deflection wires 42 spaced approximately evenly around the periphery of the catheter 40. Each deflection wire 42 can be individually advanced or be advanced together as a group. A plurality of deflection wires 42 can help increase the likelihood of properly centering the catheter 40 and guide wire 38 while providing additional stability.

As illustrated in FIGS. 3C, 3D and 3E, the deflection wire 42 can have, for example, a round cross-sectional area, an oblong or elliptical cross-sectional area, or a rectangular cross-sectional area. A ribbon-like deflection wire 42 with a rectangular, elliptical or oblong cross-sectional area will preferentially bend in one direction. The deflection wire 42 can be oriented so that the wider portion of the deflection wire 42 faces the vessel wall such that when the deflection wire 42 contacts the vessel wall, a relatively large surface area of the deflection wire 42 makes contact with the vessel wall. This allows the deflection wire 42 to spread out the force exerted on the vessel wall over a larger area.

The deflection wire 42 can be made from a variety of materials such as stainless steel, Nitinol, MP35N or other metallic materials commonly used in medical devices. Alternatively, the deflection wire 42 can be made from a polymer such as polyimide, PEEK, polypropylene or other polymer based materials commonly used in medical devices.

Figure 4A:
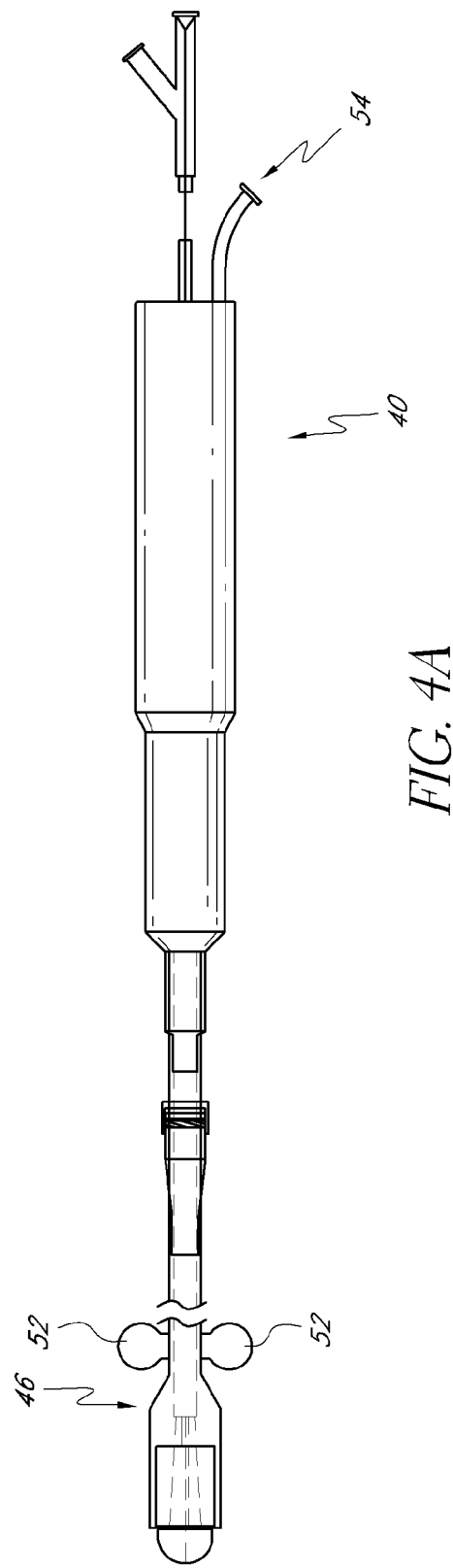
FIG. 4A is a side view of a catheter with a plurality of deflection balloons.
Figure 4B:
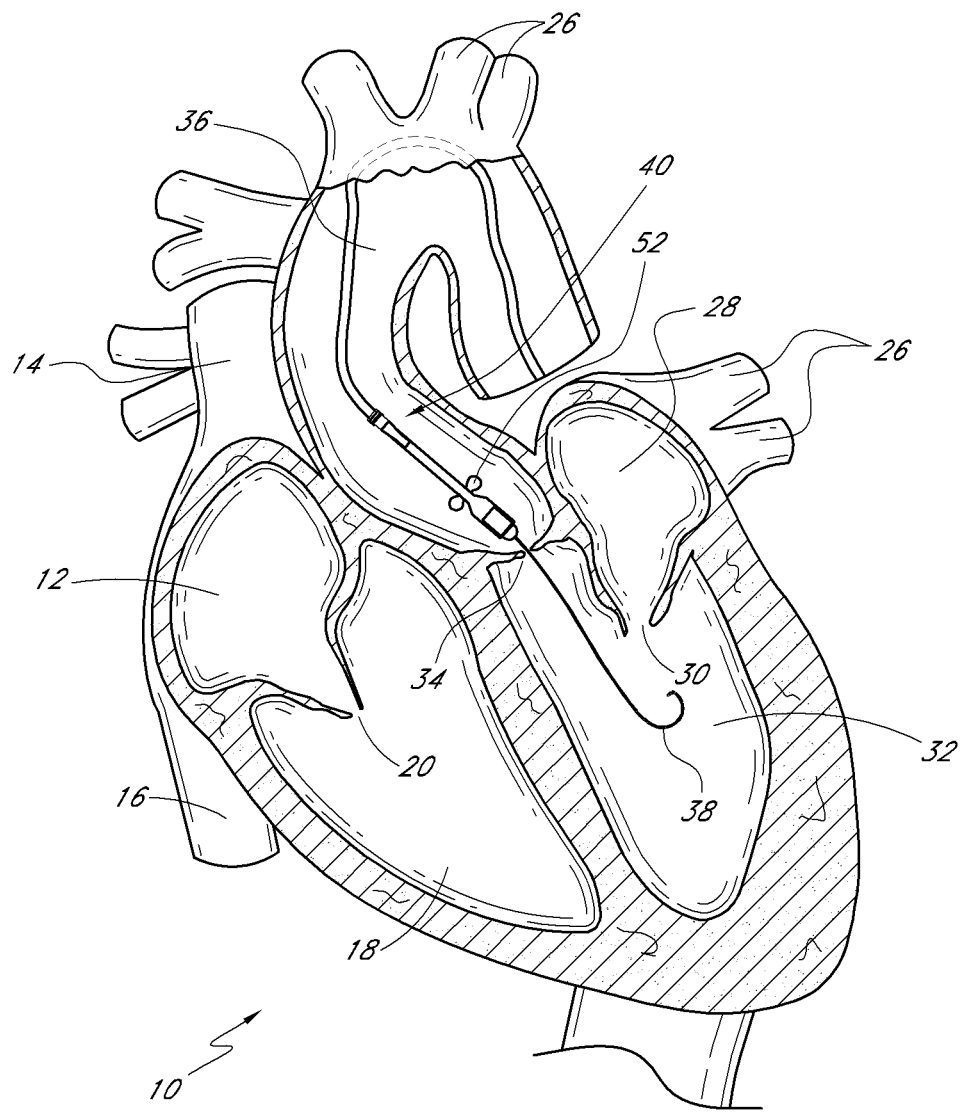
FIG. 4B is a cross-sectional view of a heart and its major blood vessels with a catheter disposed within the aorta and heart, the catheter centered within the aorta with a plurality of deflection balloons.

In another embodiment, the method and apparatus for displacing the catheter away from the vessel wall comprises a displacement balloon that is used with the catheter. For example, FIGS. 4A and 4B illustrate an embodiment of a catheter 40 having at least one displacement balloon 52 that can be inflated to displace the catheter 40 and guide wire 38 away from the vessel wall. The embodiment illustrated in FIGS. 4A and 4B comprises two displacement balloons 52 located on or near the distal portion of the catheter 40. The displacement balloons 52 can be inflated and deflated using a first inflation lumen 54 that extends from the proximal portion of the catheter 40 to the displacement balloons 52. When the displacement balloons 52 are inflated, the catheter 40 is displaced away from the blood vessel wall such that the catheter 40 and guide wire 38 are located in or can pass through the central lumen of the aortic valve 34. In other embodiments, the catheter 40 can have more or less than 2 displacement balloons. In other embodiments, the displacement balloon can be an annular balloon.

Figure 5:
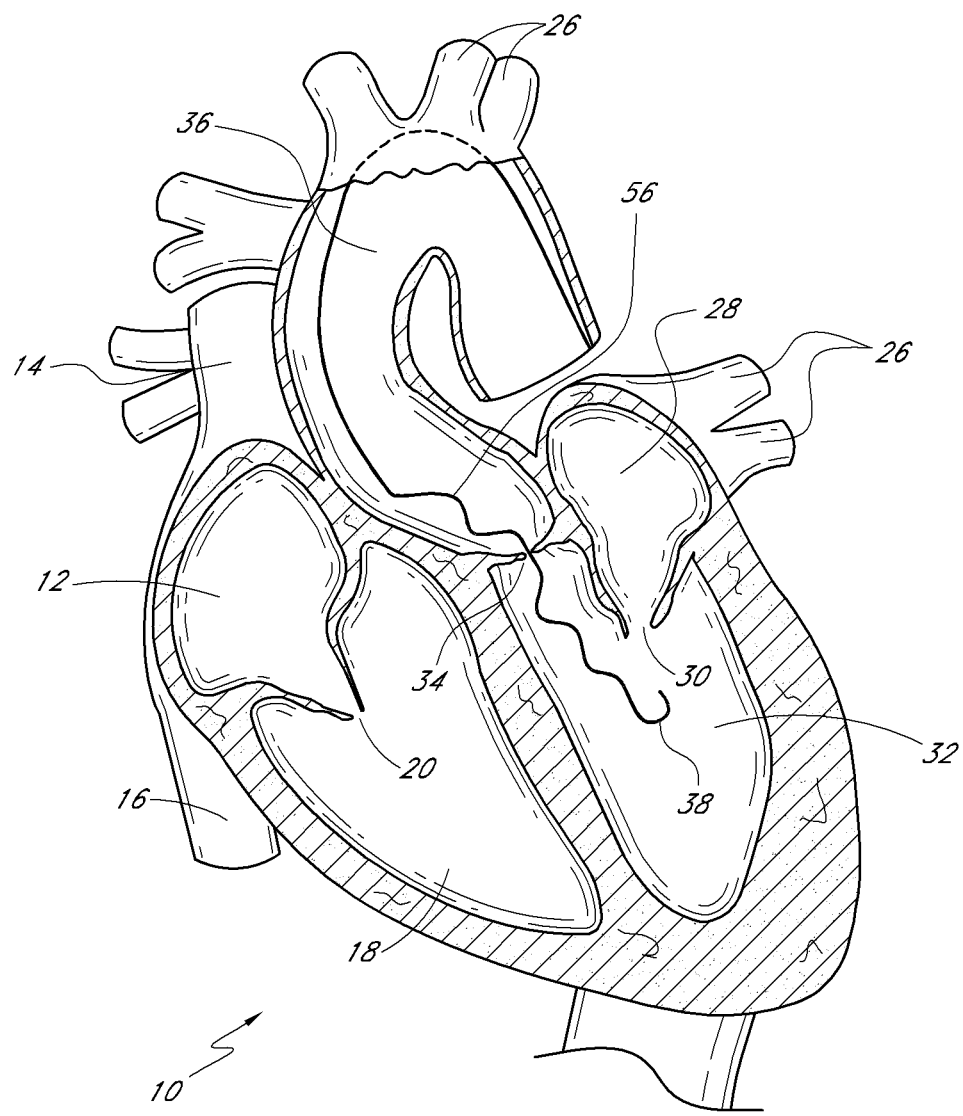
FIG. 5 is a cross-sectional view a heart and its major blood vessels with a guide wire disposed within the aorta and heart, the guide wire having a sinusoidal shape.

In another embodiment, the method and apparatus for displacing the catheter away from the vessel wall comprises using a guide wire that includes one or more bends that allow the guide wire and catheter to pass the central lumen of the aortic valve. FIG. 5 illustrates an embodiment of a guide wire 38 that is sinusoidal in shape. The sinusoidal guide wire 38 has a series of peaks 56, an amplitude between about 2 mm to 60 mm in height or between about 2 mm to 30 mm in height when measured from peak to peak, and a period between about 2 to 60 mm in length. The amplitude of the sinusoidal guide wire 38 is preferably about half the diameter of the aorta 36 or aortic valve 34 so that a peak 56 of the guide wire 38 can be located in the central lumen of the aortic valve 34 by rotating and advancing or retracting the guide wire 38 after the guide wire 38 has been inserted through the aortic valve 34.

Although the methods and devices described above have been described in connection with guiding a catheter through an aortic valve, the methods and devices described above can also be used to guide a catheter through any heart valve or blood vessel valve. In addition, the methods and devices described above can be used guide a valve implant deployment catheter so that the valve implant can be properly positioned in the patient's heart or vasculature. Embodiments of valve implants, deployment catheters and the methods of their use are more fully described in U.S. Publication No. 2005/0273160 A1 filed Apr. 22, 2005, U.S. Publication No.

2006/0025855 A1 filed May 5, 2005, and U.S. Publication No. 2007/0005133 A1 filed Jun. 7, 2006, each of which is hereby incorporated by reference in its entirety.

An example of an embodiment of a valve implant is illustrated in FIGS. 6A-6D. The implant 100 of the illustrated embodiment generally comprises an inflatable cuff or body 102, which is configured to support a valve that is coupled to the cuff 102. As will be explained in more detail below, the valve is configured to move in response to the hemodynamic movement of the blood pumped by the heart 10 between an "open" configuration where blood can throw the implant 100 in a first direction (labeled A in FIG. 6B) and a "closed" configuration whereby blood is prevented from back flowing through the valve in a second direction B (labeled B in FIG. 6B).

In the illustrated embodiment, the cuff 102 comprises a thin flexible tubular material 106 such as a flexible fabric or thin membrane with little dimensional integrity. As will be explained in more detail below, the cuff 102 can be changed preferably, in situ, to a support structure to which other components (e.g., the valve) of the implant 100 can be secured and where tissue ingrowth can occur. Uninflated, the cuff 102 is preferably incapable of providing support. In one embodiment, the cuff 102 comprises Dacron, PTFE, ePTFE, TFE or polyester fabric 106 as seen in conventional devices such as surgical stented or stent less valves and annuloplasty rings. The fabric 106 thickness may range from about 0.002 inches to about 0.020 inches of an inch depending upon material selection and weave. Weave density may also be adjusted from a very tight weave to prevent blood from penetrating through the fabric 106 to a looser weave to allow tissue to grow and surround the fabric 106 completely. Additional compositions and configurations of the cuff 102 will be described in more detail below.

Figure 6A:
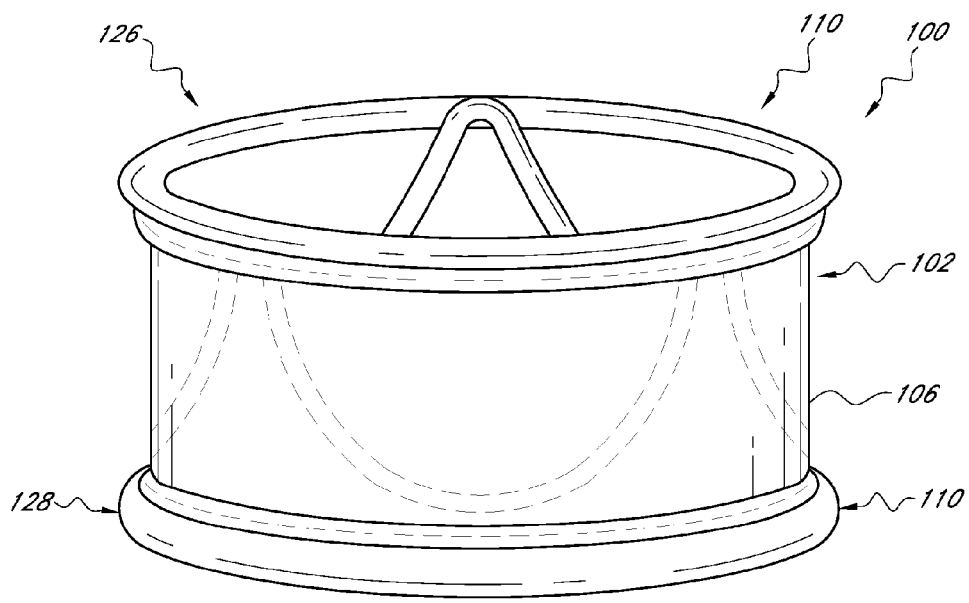
FIG. 6A is a front perspective view of an embodiment of a valve implant.
Figure 6B:
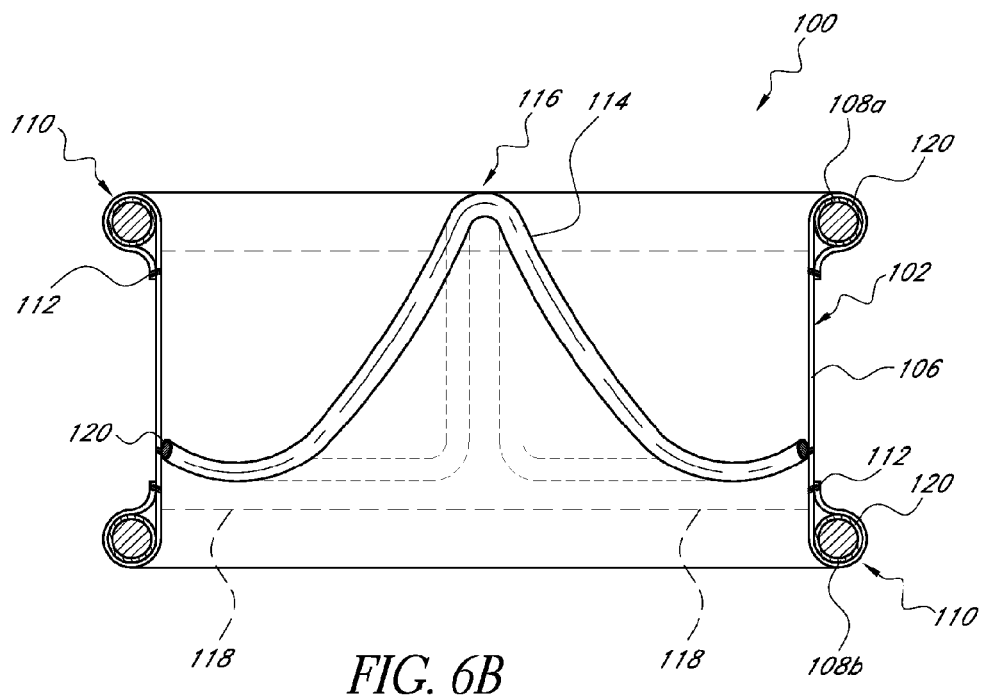
FIG. 6B is a cross-sectional side view of the implant of FIG. 6A.
Figure 6C:
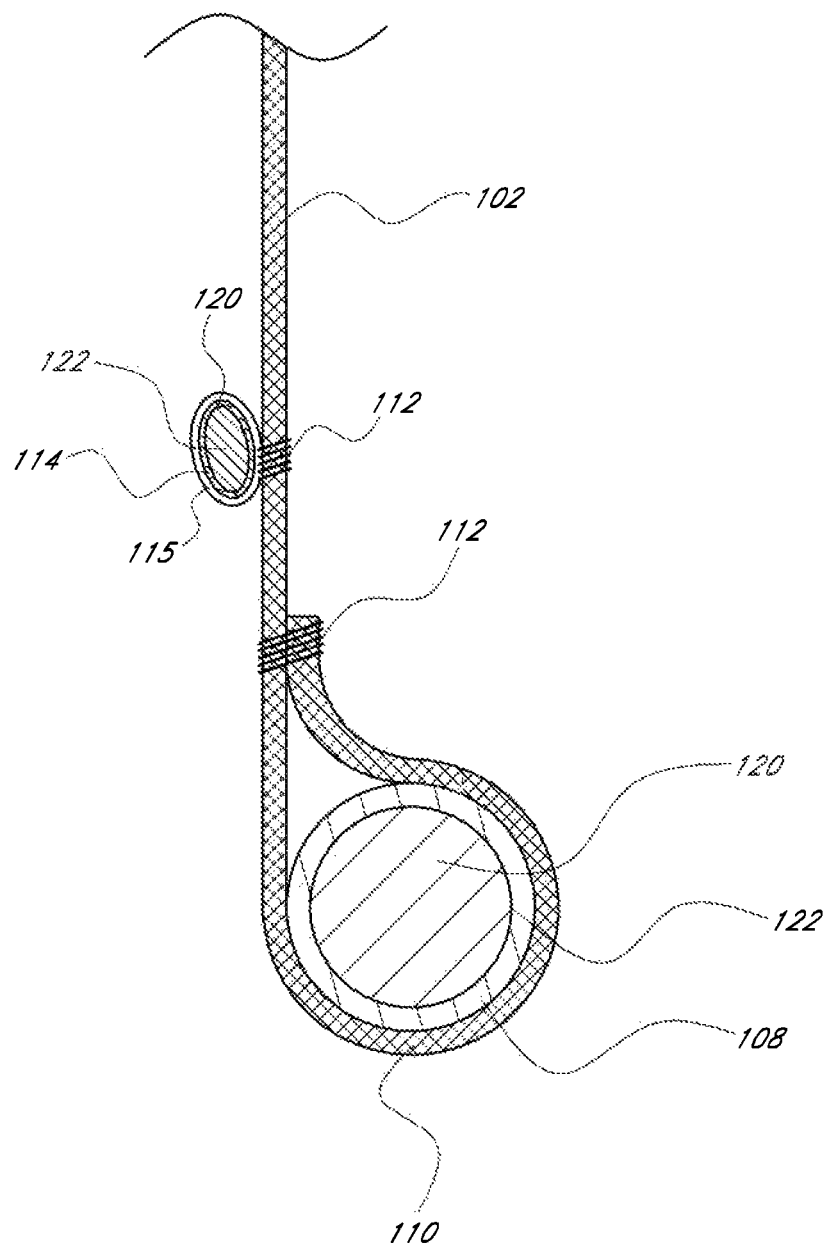
FIG. 6C is an enlarged cross-sectional view of a lower portion of FIG. 6B.
Figure 6D:
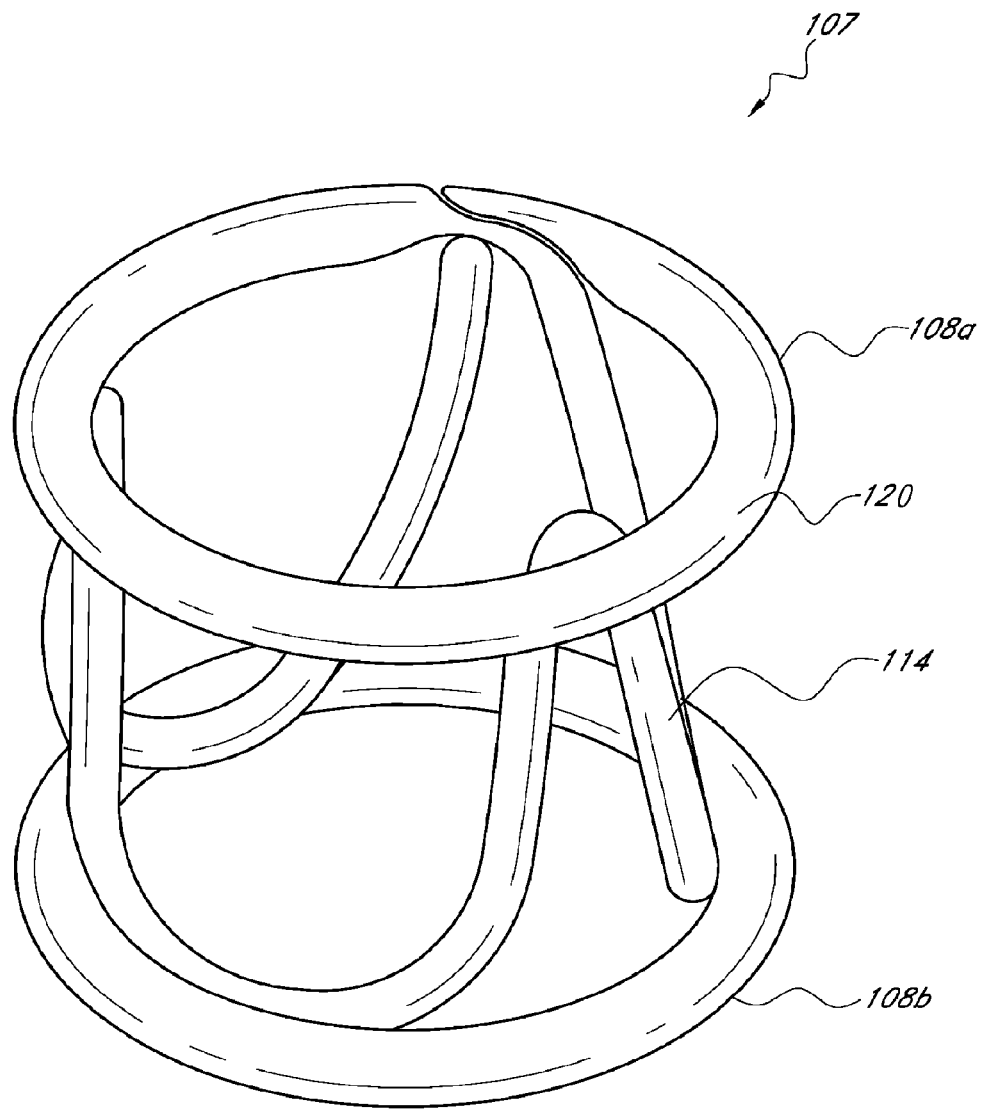
FIG. 6D is a front perspective view of an inflatable support structure of the implant of FIG. 6A.

With continued reference to FIGS. 6B-6D, in the illustrated embodiment, the implant 100 includes an inflatable structure 107 that forms one or more of inflation channels 120, which in illustrated embodiment are formed in part by a pair of distinct balloon rings or toroids 108a, 108b. The rings 108a, 108b in this embodiment are positioned at the proximal and distal ends 126, 128 of the cuff 102. As will be explained below, the rings 108 can be secured to the body 102 in any of a variety of manners. With reference to FIG. 6C, in the illustrated embodiment, the rings 108 are secured within folds 110 formed at the proximal and distal ends 126, 128 of the cuff 102. The folds 110, in turn, are secured by sutures or stitches 112. See FIG. 6C.

The illustrated inflatable structure 107 also includes inflatable struts 114, which in the illustrated embodiment are formed from an annular zig-zag pattern having three proximal bends 116 and three distal bends 118. As best seen in FIG. 6C, the struts 114 can be secured to the cuff 102 within pockets 115 of cuff material by sutures 112. Of course, as will be explained in more detail, other embodiments other configurations can be can be used to secure the struts 114 to the fabric 106.

As mentioned above, the inflatable rings 108 and struts 114 form the inflatable structure 107, which, in turn, defines the inflation channels 120. The inflation channels 120 receive inflation media 122 to generally inflate the inflatable structure 107. When inflated, the inflatable rings and struts 108, 114 provide can provide structural support to the inflatable implant 100 and/or help to secure the implant 100 within the heart. Uninflated, the implant 100 is a generally thin, flexible shapeless assembly that is preferably uncapable of support and is advantageously able to take a small, reduced profile form in which it can be percutaneously inserted into the body.

As will be explained in more detail below, in modified embodiments, the inflatable structure 107 may comprise any of a variety of configurations of inflation channels 120 that can be formed from other inflatable members in addition to or in the alternative to the inflatable rings 108 and struts 114 shown in FIGS. 6A and 6B. In addition, the inflatable media 122 and methods for inflating the inflatable structure 107 will be described in more detail below.

With particular reference to FIG. 6D, in the illustrated embodiment, the proximal ring 108a and struts 114 are joined such that the inflation channel 120 of the proximal ring 108a is in fluid communication with the inflation channel 120 of the struts 114. In contrast, the inflation channel 120 of the distal ring 108b is not in communication with the inflation channels 120 of the proximal ring 108a and struts 114. In this manner, the inflation channels of the (i) proximal ring 108a and struts 115 can be inflated independently from the (ii) distal ring 108b. As will be explained in more detail below, the two groups of inflation channels 120 are preferably connected to independent fluid delivery devices to facilitate the independent inflation. It should be appreciated that in modified embodiments the inflatable structure can include less (i.e., one common inflation channel) or more independent inflation channels. For example, in one embodiment, the inflation channels of the proximal ring 108a, struts 114 and distal ring 108b can all be in fluid communication with each other such that they can be inflated from a single inflation device. In another embodiment, the inflation channels of the proximal ring the proximal ring 108a, struts 114 and distal ring 108b can all be separated and therefore utilize three inflation devices.

With reference to FIG. 6B, in the illustrated embodiment, the proximal ring 108a has a cross-sectional diameter of about 0.090 inches. The struts have a cross-sectional diameter of about 0.060 inches. The distal ring 108b has a cross-sectional diameter of about 0.090 inches diameter.

In prior art surgically implanted valves, the valve generally includes a rigid inner support structure that is formed from polycarbonate, silicone or titanium wrapped in silicone and Dacron. These surgical valves vary in diameter for different patients due to the respective implantation site and orifice size. Generally the largest diameter implantable is the best choice for the patient. These diameters range from about 16 mm to 30 mm.

As mentioned above, the implant 100 allows the physician to deliver a valve via catheterization in a lower profile and a safer manner than currently available. When the implant 100 is delivered to the site via a delivery catheter, the implant 100 is a thin, generally shapeless assembly in need of structure and definition. At the implantation site, the inflation media 122 (e.g., a fluid or gas) may be added via a catheter lumen to the inflation channels 120 providing structure and definition to the implant 100. The inflation media 122 therefore comprises part of the support structure for implant 100 after it is inflated. The inflation media 122 that is inserted into the inflation channels 120 can be pressurized and/or can solidify in situ to provide structure to the implant 100. Additional details and embodiments of the implant 100, can be found in U.S. Pat. No. 5,554,185 to Block, the disclosure of which is expressly incorporated in its entirety herein by reference.

The body 102 of the valve implant 100 may be made from many different materials such as Dacron, TFE, PTFE, ePTFE, woven metal fabrics, braided structures, or other generally accepted implantable materials. These materials may also be cast, extruded, or seamed together using heat, direct or indirect, sintering techniques, laser energy sources, ultrasound techniques, molding or thermoforming technologies. Since the body 102 generally surrounds the inflation lumens 120, which can be formed by separate members (e.g., rings 108), the attachment or encapsulation of these lumens 120 can be in intimate contact with the body material 106 or a loosely restrained by the surrounding material 106. These inflation lumens 120 can also be formed also by sealing the body material 106 to create an integral lumen from the body 102 itself. For example, by adding a material such as a silicone layer to a porous material such as Dacron, the fabric 106 can resist fluid penetration or hold pressures if sealed. Materials may also be added to the sheet or cylinder material to create a fluid tight barrier. However, in the illustrated embodiment of FIGS. 6A and 6B, the inflation lumens 120 are formed by balloons, which form the separate inflation components 108a, 108b, 122, which are, in turn, secured to the material 106.

Various shapes of the body 102 may be manufactured to best fit anatomical variations from person to person. As described above, these may include a simple cylinder, a hyperboloid, a device with a larger diameter in its mid portion and a smaller diameter at one or both ends, a funnel type configuration or other conforming shape to native anatomies. The shape of the implant 100 is preferably contoured to engage a feature of the native anatomy in such a way as to prevent the migration of the device in a proximal or distal direction. In one embodiment the feature that the device engages is the aortic root or aortic bulb, or the sinuses of the coronary arteries. In another embodiment the feature that the device engages is the native valve annulus, the native valve or a portion of the native valve. In certain embodiments, the feature that the implant 100 engages to prevent migration has a diametral difference between 1% and 10%. In another embodiment the feature that the implant 100 engages to prevent migration the diameter difference is between 5% and 40%. In certain embodiments the diameter difference is defined by the free shape of the implant 100. In another embodiment the diameter difference prevents migration in only one direction. In another embodiment the diameter difference prevents migration in two directions, for example proximal and distal or retrograde and antigrade. Similar to surgical valves, the implant 100 will vary in diameter ranging from about 14 mm to about 30 mm and have a height ranging from about 10 mm to about 30 mm in the portion of the implant 100 where the leaflets of the valve are mounted. Portions of the implant 100 intended for placement in the aortic root may have larger diameters preferably ranging from about 20 to about 45 mm Different diameters of valves will be required to replace native valves of various sizes. For different locations in the anatomy, different lengths of valves or anchoring devices will also be required. For example a valve designed to replace the native aortic valve needs to have a relatively short length because of the location of the coronary artery ostium (left and right arteries). A valve designed to replace or supplement a pulmonary valve could have significantly greater length because the anatomy of the pulmonary artery allows for additional length.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods may be performed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments disclosed herein. Similarly, the various features and steps discussed above, as well as other known equivalents for each such feature or step, can be mixed and matched by one of ordinary skill in this art to perform methods in accordance with principles described herein. Additionally, the methods which is described and illustrated herein is not limited to the exact sequence of acts described, nor is it necessarily limited to the practice of all of the acts set forth. Other sequences of events or acts, or less than all of the events, or simultaneous occurrence of the events, may be utilized in practicing the embodiments of the invention.

Although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, the invention is not intended to be limited by the specific disclosures of preferred embodiments herein

What is claimed is:

1. A method of treating a patient with a calcified aortic valve, the method comprising:
    introducing a guide wire into a blood vessel;
    advancing the guide wire through the aorta to the aortic valve;
    advancing the guide wire through the aortic valve;
    introducing a catheter into the blood vessel over the guide wire, the catheter comprising an elongate body, a distal portion, a guide wire lumen, at least one deflection wire lumen, and at least one deflection wire residing in the at least one deflection wire lumen and having a distal end directly attached to the distal portion;
    advancing the catheter over the guide wire through the aorta;
    actuating the at least one deflection wire; and
    advancing the catheter through the aortic valve, wherein actuating the at least one deflection wire occurs prior to advancing the catheter through the aortic valve.

2. The method of claim 1, wherein the catheter further comprises a dilatation balloon.

3. The method of claim 2, further comprises inflating the dilatation balloon.

4. The method of claim 1, wherein the catheter carries an implantable prosthetic valve.

5. The method of claim 4, further comprises deploying the implantable prosthetic valve.

* * * * *